United States Patent
Tracy et al.

(10) Patent No.: US 9,766,261 B2
(45) Date of Patent: Sep. 19, 2017

(54) LOW COST OPTICAL HIGH SPEED DISCRETE MEASUREMENT SYSTEM

(71) Applicant: GnuBIO, Inc., Cambridge, MA (US)

(72) Inventors: David H. Tracy, Champaign, IL (US); Aaron Weber, Arlington, MA (US); Peter Stokes, Cambridge, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 334 days.

(21) Appl. No.: 14/289,982

(22) Filed: May 29, 2014

(65) Prior Publication Data
US 2014/0354795 A1    Dec. 4, 2014

Related U.S. Application Data

(60) Provisional application No. 61/828,597, filed on May 29, 2013.

(51) Int. Cl.
*G01P 5/20*    (2006.01)
*G01P 5/00*    (2006.01)
(Continued)

(52) U.S. Cl.
CPC .......... *G01P 5/20* (2013.01); *B01L 3/502715* (2013.01); *B01L 3/502784* (2013.01);
(Continued)

(58) Field of Classification Search
CPC ....................................................... G01P 5/20
(Continued)

(56) References Cited

U.S. PATENT DOCUMENTS 4,136,927 A * 1/1979 Lisfeld .................. G02B 21/08
                                                        359/388
5,074,658 A * 12/1991 Tavlarides ......... G01N 15/1459
                                                        356/27
(Continued)

FOREIGN PATENT DOCUMENTS

AL    2012/135201 A1    10/2012
EP        2364774 A2     9/2011
(Continued)

OTHER PUBLICATIONS

U.S. Appl. No. 14/290,867, filed May 29, 2014.
(Continued)

*Primary Examiner* — Jeffery Williams
(74) *Attorney, Agent, or Firm* — Kilpatrick Townsend and Stockton LLP (57) ABSTRACT

Systems and methods are provided for determining a velocity or an inflation rate of a droplet in a microfluidic channel. The droplet is exposed to two or more temporally separated flashes of light, each flash including light of one wavelength band, and imaged using a detector configured to distinguish light in the wavelength bands. Two or more images of the droplet are acquired, each corresponding to one of the flashes, and all within a single video frame or photographic exposure. The images can be processed separately and the position or size of the droplet in each image is calculated. A velocity or inflation rate is then determined by dividing the change in position or size by the amount of time allowed to pass between the flashes.

24 Claims, 3 Drawing Sheets

(51) Int. Cl.
   *G01F 1/708* (2006.01)
   *G01N 15/02* (2006.01)
   *B01L 3/00* (2006.01)
   *G01F 22/00* (2006.01)
   *G01N 35/08* (2006.01)
   *G01N 15/14* (2006.01)
   *G01N 15/10* (2006.01)

(52) U.S. Cl.
   CPC ............ *G01F 1/7086* (2013.01); *G01F 22/00* (2013.01); *G01N 15/0227* (2013.01); *G01N 15/1434* (2013.01); *G01N 15/1459* (2013.01); *G01N 15/1463* (2013.01); *G01N 15/1484* (2013.01); *G01P 5/001* (2013.01); *B01L 2200/143* (2013.01); *B01L 2400/0487* (2013.01); *B01L 2400/082* (2013.01); *G01N 35/08* (2013.01); *G01N 2015/1075* (2013.01); *G01N 2015/1493* (2013.01)

(58) Field of Classification Search
   USPC .......................................................... 348/79
   See application file for complete search history.

(56) References Cited

U.S. PATENT DOCUMENTS

| | | | |
|---|---|---|---|
| 8,528,589 | B2 | 9/2013 | Miller et al. |
| 8,535,889 | B2 | 9/2013 | Larson et al. |
| 2002/0145726 | A1 | 10/2002 | Chao et al. |
| 2003/0112505 | A1 | 6/2003 | Nihoshi |
| 2006/0175561 | A1 | 8/2006 | Estevadeordali et al. |
| 2008/0274905 | A1* | 11/2008 | Greene .............. G01N 21/6428 506/4 |
| 2011/0151578 | A1 | 6/2011 | Abate et al. |
| 2011/0218123 | A1 | 9/2011 | Weitz et al. |
| 2011/0250597 | A1 | 10/2011 | Larson et al. |
| 2011/0267457 | A1 | 11/2011 | Weitz et al. |
| 2011/0306853 | A1* | 12/2011 | Black .................. A61B 5/1468 600/309 |
| 2011/0312626 | A1* | 12/2011 | Azimi ................... B01L 3/5027 506/39 |
| 2012/0015822 | A1 | 1/2012 | Weitz et al. |
| 2012/0052560 | A1* | 3/2012 | Knight .............. B01L 3/502784 435/286.1 |
| 2012/0132288 | A1 | 5/2012 | Weitz et al. |
| 2012/0219947 | A1 | 8/2012 | Yurkovetsky et al. |
| 2012/0220494 | A1 | 8/2012 | Samuels et al. |
| 2012/0222748 | A1 | 9/2012 | Weitz et al. |
| 2012/0309002 | A1 | 12/2012 | Link |

FOREIGN PATENT DOCUMENTS

| | | |
|---|---|---|
| EP | 2662135 A2 | 11/2013 |
| WO | 2007/081385 A2 | 7/2007 |
| WO | 2007/081387 A1 | 7/2007 |
| WO | 2013/165748 A1 | 7/2011 |
| WO | 2012/078710 A1 | 6/2012 |
| WO | 2012/135237 A1 | 10/2012 |
| WO | 2012/135259 A1 | 10/2012 |
| WO | 2013/095737 A2 | 6/2013 |
| WO | 2013/122826 A1 | 8/2013 |
| WO | 2014/043388 A1 | 3/2014 |
| WO | 2014/093976 A1 | 6/2014 |
| WO | 2014/117088 A1 | 7/2014 |

OTHER PUBLICATIONS

U.S. Appl. No. 14/470,860, filed Aug. 27, 2014.
U.S. Appl. No. 14/502,948, filed Sep. 30, 2014.
International Appl. No. PCT/US2014/035730, filed Apr. 28, 2014, in the name of GnuBio, Inc.
Nguyen NT et al: "Optical detection for droplet size control in microfluidic droplet-based analysis systems", Sensors and Actuators B: Chemical: International Journal Devoted to Research and Development of Physical and Chemical Transducers. Elsevier BV, NL, vol. 117, No. 2, Oct. 12, 2006 (Oct. 12, 2006), pp. 431-436.
Extended European Search Report dated Nov. 17, 2016 in EP Patent Application No. 148047384, all pages.
International Search Report and Written Opinion of PCT/US2014/039942 dated Dec. 2, 2014, all pages.

* cited by examiner

LOW COST OPTICAL HIGH SPEED DISCRETE MEASUREMENT SYSTEM

CROSS-REFERENCES TO RELATED APPLICATIONS

This application claims the benefit of U.S. Provisional Patent Application No. 61/828,597, entitled "Low Cost Optical High Speed Discrete Measurement System" and filed on May 29, 2013, which is incorporated herein by reference in its entirety.

BACKGROUND OF THE INVENTION

Microfluidic methods involve passing small volumes of fluid through microfabricated structures and manipulating these volumes to carry out biological or chemical reactions. To stage such reactions, samples, reactants, solvents, or other reagents can be encapsulated in discrete droplets having volumes on the order of nanoliters or less. A droplet is typically immersed in a carrier fluid from which it is phase-separated, and transported along with the carrier fluid through microfluidic channels. In sufficiently small channels, this transport occurs at low Reynolds number and exhibits laminar flow. Reactions can be facilitated by, for example, merging droplets (causing droplet fusion), splitting droplets (causing droplet fission), injecting material into droplets, or extracting material from droplets.

To control the movement of droplets in a microfluidic device, it can be useful to measure the velocity of droplets in real time as they pass through microfluidic channels. Similarly, for droplets subject to injection or extraction of material, it can be useful to measure changes in droplet volume on short timescales. These measurements can be fed back to systems governing the flow rate of the carrier fluid or the manipulation of droplets, allowing optimization of droplet-based reactions. Measuring changes in droplet location or size is challenging, however, because of the small dimensions of microfluidic devices and the droplets themselves. Imaging individual droplets with conventional optics requires a high level of magnification and a limited field of view. A droplet traveling through a microfluidic channel at typical velocities can traverse the field of view faster than two images of the droplet can be acquired in consecutive video frames. To obtain two or more images of the same droplet and measure a change, more sophisticated optics can be employed to expand the field of view, or a high-speed camera can be used instead of a conventional video camera. These solutions are expensive and difficult to implement.

BRIEF SUMMARY OF THE INVENTION

The present disclosure generally pertains to a system for determining the velocity or inflation rate of a moving object, and a method for using a color camera to determine the velocity or inflation rate. In some instances, the system and method are applied to measure the speed of droplets flowing in a microfluidic channel.

The system includes a multicolor light source, located on one side of the object, and an optical microscope, monitored by a camera or detector, on the other. The camera is focused on the object; the light source is defocused so that it illuminates the object without yielding an image of the light source itself on the camera.

During a single camera exposure, the object, whose velocity is to be measured, is illuminated successively with multiple flashes of light, each of a different color. The camera captures multiple images of the subject, in different colors, overlaid in the exposure. Knowing the colors of the illumination, one can deduce the three images of the object, spatially separated in proportion to the time between flashes. The spatial separation and the known timing of the flashes can yield a velocity measurement for the object.

In a first aspect of the present invention, a system is provided for determining a velocity or an inflation rate of a droplet passing through a microfluidic channel. The system includes a multicolor light source configured to emit light in (i) two or more different wavelength bands and (ii) temporally separated flashes, so that each flash includes light of only one of the wavelength bands; a detector configured to detect and distinguish between light in the wavelength bands; and a microfluidic channel disposed in a translucent material. The multicolor light source, the detector, and the microfluidic channel are positioned such that light emitted by the multicolor light source is incident upon the microfluidic channel, and a droplet passing through the microfluidic channel and illuminated by the multicolor light source is imaged on the detector.

In some embodiments of the system, the multicolor light source is a multicolor LED. In some embodiments, the multicolor LED is a three-color LED, such as a red-green-blue (RGB) LED or a red-green-yellow (RGY) LED.

In some embodiments of the system, the detector includes a charge-coupled device (CCD) or a complementary metal-oxide-semiconductor (CMOS) image sensor. In some embodiments, the detector is configured to detect light in two or more color channels, each color channel corresponding to one of said wavelength bands. The detector includes a filter in some embodiments, where the filter is configured to pass light in at least one of the wavelength bands. The filter can be a multiband filter configured to pass light in the two or more wavelength bands.

In some embodiments, the system also includes a source aperture interposed between the multicolor light source and the microfluidic channel. In some embodiments, the system also includes a microscope interposed between the microfluidic channel and the detector. The microscope can include a first lens, a second lens, and an aperture stop interposed between the first lens and the second lens. The multicolor light source, the first lens of the microscope, and the aperture stop of the microscope can be positioned such that light from the multicolor light source is focused at the aperture stop of the microscope.

In some embodiments, the system also includes a pressure source coupled to the microfluidic channel.

In a second aspect of the present invention, a method is provided for determining a velocity or an inflation rate of a droplet passing through a microfluidic channel using the system described above. The method includes the following steps: illuminating the droplet with a first flash of light emitted by the multicolor light source, wherein the first flash of light includes light of a first wavelength band; acquiring a first image of the droplet when the droplet is illuminated with the first flash of light; allowing an amount of time to pass; illuminating the droplet with a second flash of light emitted by the multicolor light source, wherein the second flash of light includes light of a second wavelength band different from the first wavelength band; acquiring a second image of the droplet when the droplet is illuminated with the second flash of light, wherein the first image and the second image are acquired (i) using the detector and (ii) as part of the same video frame or the same photographic exposure; calculating a change in position or size of the droplet between the first image and the second image; and dividing the change in position or size of the droplet by the amount of time, thereby determining a velocity or an inflation rate of the droplet passing through the microfluidic channel between the first image and the second image.

In some embodiments of the method, calculating a change in position or size of the droplet between the first image and the second image comprises separating the first image from the second image in the video frame or the photographic exposure.

In some embodiments, the method includes determining a velocity of the droplet. In these embodiments, calculating the change in position of the droplet can include determining a first centroid position of the droplet in the first image and a second centroid position of the droplet in the second image. Alternatively, or in addition, calculating the change in position of the droplet can include determining a first leading or trailing edge position of the droplet in the first image and a second leading or trailing edge position of the droplet in the second image.

In embodiments of the method that include determining an inflation rate of the droplet, calculating a change in size of the droplet between the first image and the second image includes determining a first diameter of the droplet in the first image and a second diameter of the droplet in the second image.

In some embodiments, the system further comprises a pressure source coupled to the microfluidic channel, and the method further comprises adjusting the pressure source based upon the velocity or the inflation rate of the droplet.

The method also includes the following additional steps in some embodiments: illuminating the droplet with a third flash of light emitted by the multicolor light source; acquiring a third image of the droplet when the droplet is illuminated with the third flash of light, wherein the image is acquired using the detector; selecting a reference image, which is either the first image or the second image; calculating an additional change in position or size of the droplet between the reference image and the third image; determining an elapsed time between acquisition of the reference image and acquisition of the third image; and dividing the additional change in position or size of the droplet by the elapsed time to determine a velocity or an inflation rate of the droplet in the microfluidic channel between the reference image and the third image. When these additional steps are included, the third flash of light can include light of a third wavelength band different from the first wavelength band and the second wavelength band. The third image and the reference image can be acquired as part of the same video frame or the same photographic exposure. In some embodiments, the elapsed time between acquisition of the reference image and acquisition of the third image differs by a factor of at least 2 from the amount of time allowed to pass between acquisition of the first image and acquisition of the second image.

DETAILED DESCRIPTION OF THE INVENTION

I. Overview

The inventors have surprisingly discovered that the velocity or inflation rate of a droplet in a microfluidic channel can be determined by acquiring multiple images of the droplet within a single video frame or photographic exposure. Each of these images results from illumination of the droplet with light of a different color. A multicolor light source is configured to illuminate the droplet with multiple flashes of light, each of a different color and occurring at a different time, while a camera is capturing the frame or exposure. The colors can be matched to color channels of the camera, so the images can be separated from each other by image processing after capture. Positions or sizes of the droplet in each image can then be calculated, and, with knowledge of the times between the flashes, the velocity or inflation rate of the droplet can be determined. Each flash is short enough that the droplet does not move significantly during the illumination and a sharp image is obtained. The amount of time between flashes can be varied to allow observation of changes in the droplet over different time scales, and to prevent confusion between different droplets moving through the microfluidic channel in series.

II. Definitions

"Velocity" refers to the directed rate of movement of an object. In the case of a microfluidic droplet, velocity can be specified in terms of the rate and direction the droplet is moving within a channel (e.g., 10 µm/s to the right or 50 µm/s downstream). Velocity can be measured or specified with reference to the object as a whole, a portion of the object, or a point on the object, for example the center or the trailing edge.

"Inflation rate" refers to the rate at which the volume of an object changes. A positive inflation rate implies increasing volume or growth, while a negative inflation rate implies decreasing volume or shrinkage. Inflation rate can be inferred from changes in various dimensions of an object, such as its width or diameter.

"Microfluidic channel" refers to channel or vessel, no more than about five millimeters across in its narrowest dimension, for carrying or holding a fluid.

"Wavelength band" refers to a continuous, closed-ended range of wavelengths of light. The difference in wavelength between the endpoints of wavelength band is said to be the width of the wavelength band. A sample of light is said to fall within a wavelength band or overlap a wavelength band if the sample has measurable intensity for at least one wavelength within the wavelength band. Two wavelength bands are said to be different if they are defined by different ranges of wavelengths, or if one wavelength band encompasses wavelengths of light not encompassed by the other wavelength band. Two wavelength bands are said to overlap if at least one wavelength of light is common to their respective ranges. Different wavelength bands can overlap.

"Image" refers to a virtual representation of one or more objects.

"Frame" refers to the basic unit of recording of a video camera. "Exposure" refers to the basic unit of recording of a still camera. These terms can be used interchangeably in contexts where an aspect of recording or image acquisition is general to video and still photography.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

III. Systems

Figure 1:
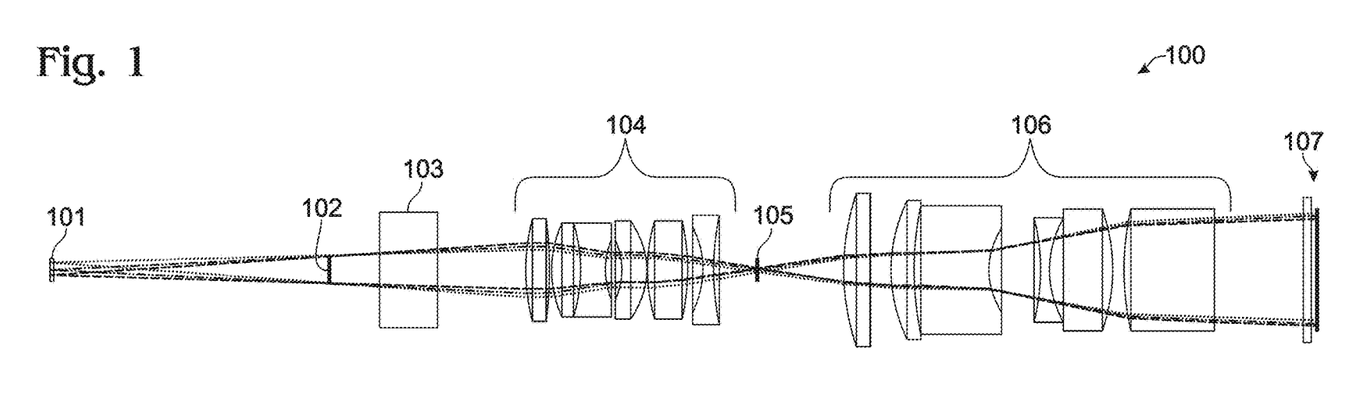
FIG. 1 shows the path of light from the multicolor light source to the detector in a system according to some embodiments of the invention.
Figure 2:
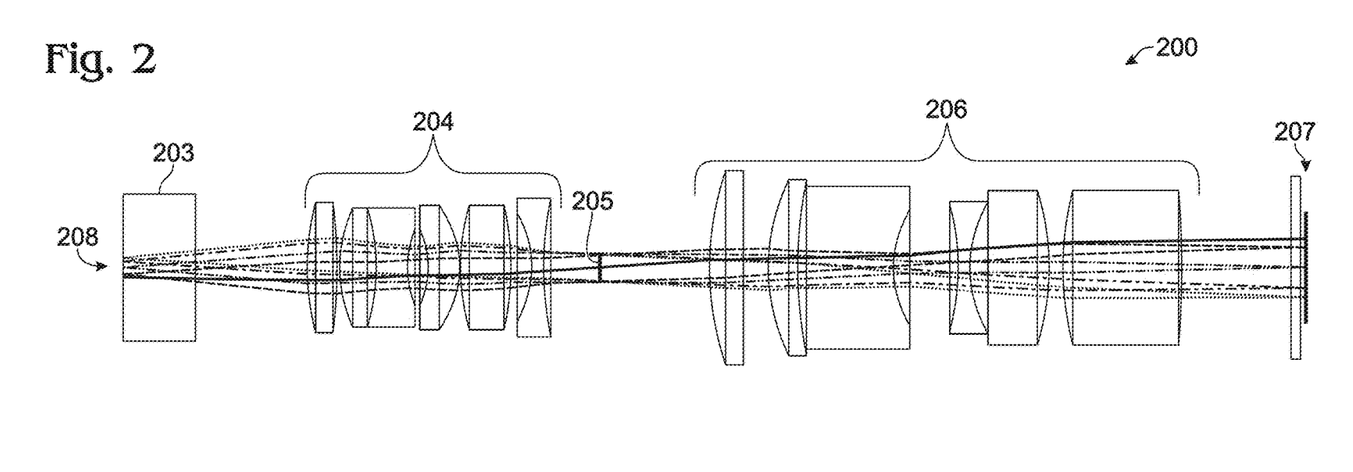
FIG. 2 shows the path of light from one or more illuminated droplets to the detector in a system according to some embodiments of the invention.

Provided herein are systems for determining a velocity or an inflation rate of a droplet passing through a microfluidic channel. Systems according to some embodiments of the invention are shown in FIGS. 1 and 2. A system 100, 200 as described below can include: a multicolor light source 101 configured to emit light in (i) two or more different wavelength bands and (ii) temporally separated flashes, wherein each flash comprises light of only one of said wavelength bands; a detector 107, 207 configured to detect and distinguish between light in said wavelength bands; and a microfluidic channel 208 disposed in a translucent material 103, 203. The multicolor light source, the detector, and the microfluidic channel are positioned such that light emitted by the multicolor light source is incident upon the microfluidic channel, and a droplet passing through the microfluidic channel and illuminated by the multicolor light source is imaged on the detector.

The multicolor light source 101 can be any light source that emits light in two or more different wavelength bands and in temporally separated flashes. In some embodiments, the multicolor light source is a multicolor light-emitting diode (LED). In some embodiments the multicolor light source is a three-color LED, such as a red-green-blue (RGB) LED or a red-green-yellow (RGY) LED. In some embodiments the multicolor light source is a four-color LED, such as a red-green-blue-white (RGBW) LED. An LED can be advantageous in the present systems because the individual LED dies, each giving rise to light in one wavelength band, are located in close proximity to each other. Thus, a single set of optics handles light of all wavelength bands, with no realignment required to switch between bands, and minimal imaging artifacts. Other possible multicolor light sources include a grouping of incandescent light bulbs, each with a color filter, or a grouping of lasers.

In some embodiments, each wavelength band corresponds to a different color, such as red, green, or blue, and light emitted in the different wavelength bands can be distinguished by eye. All else being equal, light from two wavelength bands is generally easier to distinguish, both by eye and using a detector, when the wavelength bands are narrower and the amount of overlap between them is smaller. However, non-overlapping wavelength bands are not required in the present systems. In some embodiments, each different wavelength band is at most about 300, 200, 100, 50, 40, 30, 20, or 10 nm wide. In some embodiments, any two of the two or more different wavelength bands overlap by at most about 300, 200, 100, 50, 40, 30, 20, or 10 nm. Imaging is discussed herein in terms of colors of the visible light, but wavelength bands outside the visible spectrum can also be used to image microfluidic droplets and other moving objects. For example, a multicolor light source can emit light at wavelengths corresponding to the infrared, visible, and/or ultraviolet portions of the electromagnetic spectrum.

The multicolor light source is configured to emit light in flashes of brief duration. Preferably, each flash lasts less than the amount of time needed to capture a frame using a conventional video camera. Under various video recording standards, this amount of time is about ¹/₂₄, ¹/₂₅, ¹/₃₀, or ¹/₁₀₀ of a second. More preferably, each flash lasts less than half or a third of this amount of time, so that multiple flashes can occur during capture of each frame. Each flash should be bright enough to form a clear image of the droplet on the detector under ambient lighting conditions.

Any detector 107, 207 can be used that is configured to detect light in the wavelength bands emitted by the multicolor light source, and distinguish between light in these wavelength bands. The detector can be part of a video camera or a still camera. In principle, the detector can be photographic film, although in practice digital image sensors allow for faster and more straightforward image processing and are preferred. In some embodiments the detector includes a charge-coupled device (CCD) or a complementary metal-oxide-semiconductor (CMOS) image sensor. Variants of and alternatives to these types of image sensors will be apparent to those of skill in the art.

In some embodiments, the detector detects light in two or more color channels, such as a red channel, a green channel, and/or a blue channel. Channel-wise detection can be achieved by preparing the detector as a two-dimension array of pixels, for example, with every pixel sensitive to only one color, and the pixels arranged in a repeating pattern. In some cases, pixels are arranged in 2×2 blocks in a Bayer filter mosaic, with two pixels in each block sensitive to green light, one pixel sensitive to blue light, and one pixel sensitive to red light. Alternative color filter arrays, such as red-green-blue-emerald (RGBE), cyan-yellow-green-magenta (CYGM), and red-green-blue-white (RGBW) filters, can be employed to detect and distinguish light in three, four, or more colors, including light outside of the visible spectrum. Regardless of their physical configuration, all pixels sensitive to a particular color contribute to the image detected in one color channel. Upon capture of one frame or exposure with the detector, the images obtained in all color channels can be combined or can be handled separately.

The multicolor light source and detector in the present systems are chosen together, so that the colors of the light source match the colors to which the detector is sensitive. As is discussed below, this matching allows the image generated by each flash of the multicolor light source to be recorded in only one color channel of the detector. Thus, each captured frame or exposure from the detector can be decomposed into the constituent color channel images, which can be correlated with the timing of the flashes.

To achieve better matching between the different wavelength bands of emitted light and the detector's color channels, one or more filters are employed in some embodiments. The filters can be included as part of the detector or placed in front of the detector, to receive light passed through the microfluidic channel. Each filter can cover or span the entire detector or a portion of the detector, for example a single pixel. Each filter can reduce the range of wavelengths, or the intensity of light at certain wavelengths, that reaches the detector from a single flash of the multicolor light source, thereby reducing cross-talk or bleed-through between detector color channels. As desired, the filters can be high-pass, low-pass, band-pass, multi-band, or a combination thereof. In some embodiments, the detector includes a filter configured to pass light in at least one of the wavelength bands in which the multicolor light source emits light. In some embodiments, the detector comprises a multiband filter configured to pass light in the two or more wavelength bands in which the multicolor light source emits light.

The microfluidic channel 208 employed in the present systems is disposed in a translucent material 103, 203, so that light from the multicolor light source can pass through the channel and reach the detector. Thus, a droplet traveling through the channel can be imaged on the detector. The microfluidic channel can be of any dimensions and can be part of a larger microfluidic device, such as a chip.

The present systems can be elaborated with additional optics. In some embodiments, a source aperture 102 is placed between the multicolor light source and the microfluidic channel. The source aperture limits the angular extent of emitted light that can pass through the remainder of the system, and can reduce the amount of background light reaching the detector. The source aperture can be an iris, diaphragm, pinhole, or any other kind of structure that blocks light deviating from a path between the multicolor light source and the microfluidic channel.

In some embodiments, a microscope is placed between the microfluidic channel and the detector. The microscope focuses an image of the microfluidic channel, and/or any droplet it contains, on the detector, while defocusing the multicolor light source. The microscope can include a first lens 104, 204, a second lens 106, 206, and an aperture stop 105, 205 interposed between the first lens and second lens.

Any converging lenses appropriate for the geometry of the system can be used for the first lens and second lens of the microscope. Compound lenses are shown in FIGS. 1 and 2, but simpler lenses can be used instead. It will be recognized that the focal lengths and sizes of the lenses should be chosen with other features of the system in mind, such as: the distances among the multicolor light source, microfluidic channel, and detector; the width of the detector; and the amount of scattering or refraction that occurs as light passes through the microfluidic channel.

The aperture stop between the first and second lenses can be similar in construction to the source aperture and improves the depth of focus of microfluidic droplets imaged on the detector. The aperture stop also blocks extraneous light originating at the multicolor light source from continuing through the system, thereby reducing background light levels at the detector. As shown in FIG. 1, in some embodiments the multicolor light source, the first lens of the microscope, and the aperture stop of the microscope are positioned such that light from the multicolor light source is focused at the aperture stop of the microscope. In these embodiments, any structures in the multicolor light source such as LED dies or incandescent filaments are focused at this point rather than at the detector.

FIG. 1 is a ray trace diagram for light emitted by the multicolor light source 101 (a multicolor LED) in one embodiment of the complete system. Light exits the LED and passes through a source aperture 102. The light then reaches a flow channel in a microfluidic chip 103, which is transparent, and illuminates the droplets flowing in the chip. Next, light from the LED passes through the first lens 104 in the microscope and is focused to a spot to pass through the aperture stop 105. Finally, the light passes through the second lens 106 and is defocused so that the individual LED dies are not imaged onto the detector 107.

FIG. 2 is a ray trace diagram for light reflected or transmitted by the illuminated droplets in the microfluidic chip of FIG. 1, as this light passes through the rest of the system. The first lens 204 collimates the light coming from the droplets and sends the light through the aperture stop 205. The second lens 206 then forms an image of the illuminated droplets at the detector 207.

In some embodiments, the system also includes a pressure source coupled to the microfluidic channel. The pressure source can control the speed at which droplets and carrier fluid pass through the channel, and, in conjunction with other equipment and fluid sources connected to the channel, the rate at which droplets increase or decrease in size. Based upon the velocity or inflation rate of a droplet passing through the microfluidic channel, determined according to the methods described below, the pressure can be adjusted. The result is that the system can accommodate feedback from the optical measurements to achieve a target velocity or inflation rate. The pressure source can be controlled as desired, for example with a computer or manually. If desired, the pressure source can be controlled automatically using inputs from the detector.

IV. Methods

Methods provided herein for determining a velocity or an inflation rate of a droplet passing through a microfluidic channel make use of the systems described above. The basic method involves the following steps: illuminating the droplet with a first flash of light emitted by the multicolor light source, wherein the first flash of light includes light of a first wavelength band; acquiring a first image of the droplet when the droplet is illuminated with the first flash of light; allowing an amount of time to pass; illuminating the droplet with a second flash of light emitted by the multicolor light source, wherein the second flash of light includes light of a second wavelength band different from the first wavelength band; acquiring a second image of the droplet when the droplet is illuminated with the second flash of light, wherein the first image and the second image are acquired (i) using the detector and (ii) as part of the same video frame or the same photographic exposure; calculating a change in position or size of the droplet between the first image and the second image; and dividing the change in position or size of the droplet by the amount of time, thereby determining a velocity or an inflation rate of the droplet passing through the microfluidic channel between the first image and the second image. These steps can be performed in the order in which they are listed, or in a different order, as appropriate for obtaining desired information about the moving droplet.

In each illumination step, the droplet is illuminated for enough time to acquire a clear image, but not so long that the droplet moves significantly during the illumination. In some embodiments, the duration of the flash is set so that the droplet, or a part thereof, appears to move by no more than one pixel on the detector during image acquisition. It will be recognized that an appropriate duration of the flash depends on the intensity of the multicolor light source, the level of ambient light, and the optical configuration of the system. Any of these factors can be adjusted as desired to obtain clear images of the moving droplet. The appropriate duration of the flash also depends on the velocity or inflation rate of the droplet, which may not be known to a good approximation before carrying out the method. Accordingly, flash durations can be set empirically.

The amount of time allowed to pass between acquisition of the first and second images is preferably longer than the duration of each flash. For example, the amount of time can be at least about 2, 5, 10, 20, 50, or 100 times longer than the duration of each flash. Enough time is allowed to pass between flashes to allow observation of a measurable change in the droplet, such as a change in position or size, but not enough time passes for the droplet to move out of the field of view of the detector. In some embodiments, the droplet moves by about its own width during the time between acquisition of the first and second images. It will be recognized that allowing longer amounts of time to pass between acquiring the images can afford more precise measurements of average droplet velocity or inflation rate, because the amount of change in droplet position or size is typically larger. However, such longer amounts of time can also lead to difficulty in assigning images to droplets, if multiple droplets are passing through the microfluidic channel and appear in the field of view at once. Longer amounts of time also require longer video frames or photographic exposures, which can lead to more background light entering the frame or exposure. In some embodiments, the amount of time between acquisition of the first and second images is at most about 90%, 80%, 70%, 60%, 50%, 40%, 30%, 20% 10%, or 5% of the time needed to capture one video frame or photographic exposure. In some embodiments, the amount of time is at most about 200, 100, 50, 20, 10, 5, 2, or 1 millisecond(s). An appropriate amount of time between acquisition of the first and second images can be determined empirically or otherwise, and can be measured or imposed as desired.

The multicolor light source and the detector are configured to operate in concert, such that the first flash and second flash are emitted by the light source during capture of the same video frame or photographic exposure by the detector. To establish this configuration, the multicolor light source and detector can be controlled as desired. For example, they can be coupled to each other using mechanical, electronic, and/or computational means. In some embodiments, the multicolor light source and detector together use circuitry or mechanisms adapted from conventional flash photography to assure correct flash timing. In some embodiments, the multicolor light source and detector are under the common control of a computer, which can be programmed by a person carrying out the method. Such a computer can also perform image processing.

Calculation of a change in position or size of the droplet between the first image and the second image can be performed as desired. In preferred embodiments, the first image and second image are processed or analyzed separately. For example, a position or size is computed for the droplet in each image, and then the computed values are compared to calculate a change. Each image is acquired upon illumination of the droplet with light of a distinct color, and so the images can be separated from each other, or kept separate, on the basis of the colors they contain. In some embodiments, the images are extracted from the video frame or photographic exposure in which they were acquired. This can be done, for example, by decomposing the frame into images from each color channel of the detector, or by applying a color filter to the frame in software. Alternatively, the images from each color channel can be saved or recorded separately before integration into a multicolor frame.

Processing or analyzing the first and second images separately facilitates calculation of changes in the position or size of the droplet on short time scales. This is because the droplet does not move very far in the microfluidic channel, or in the field of view of the detector, on short time scales. If only a small amount of time is allowed to pass between acquisition of the first and second images, and the images are then integrated (i.e., overlaid) into a single frame, the droplet can appear in the frame in two overlapping positions. The overlap can complicate efforts to characterize the droplet using automated image processing algorithms. For example, an algorithm that recognizes a circular object and then calculates a centroid position or diameter can fail when presented with two overlapping circles. Algorithms can also fail when applied to frames where the droplet appears in two non-overlapping positions. For example, an algorithm that expects to see a single circle can return inaccurate information if it sees another circle nearby. These problems can be avoided by separating the frame into its constituent images on the basis of color, or foregoing integration of the images. In each constituent image, the droplet appears as a single structure, with no other structures nearby and no overlap between structures. Thus, the droplet's position or size can be accurately calculated in each image.

Figure 3A:
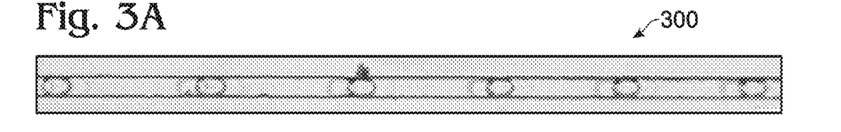
FIG. 3A is a single camera exposure of several droplets in a microfluidic channel, regularly spaced and all traveling from left to right at the same speed, being illuminated by a series of flashes from red, green and blue LEDs.
Figure 3B:
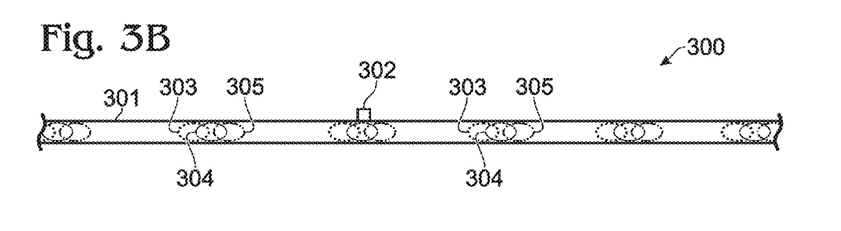
FIG. 3B is a schematic drawing of the exposure in FIG. 3A.
Figure 4A:
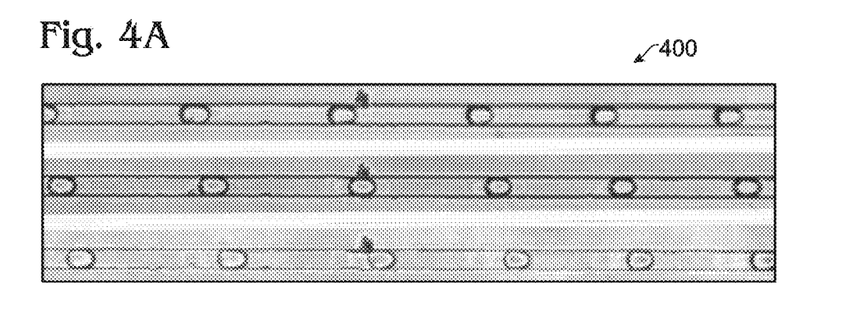
FIG. 4A shows the exposure of FIG. 3A separated into red, green and blue color channels.
Figure 4B:
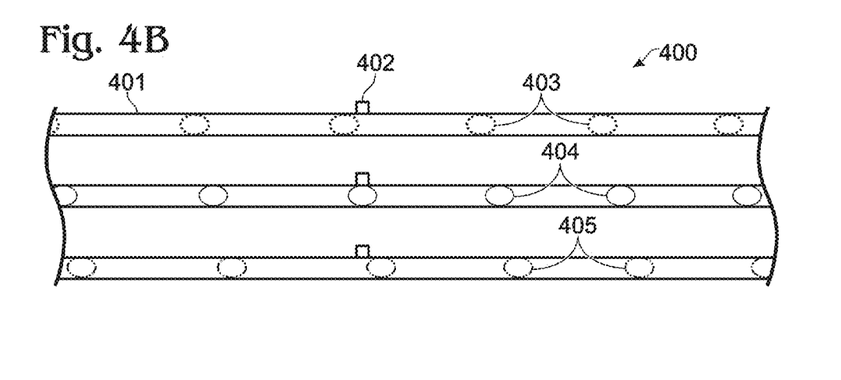
FIG. 4B is a schematic drawing of the images in FIG. 4A.

The benefits of illuminating a droplet with multiple colors of light, and acquiring a separate image for each color, can be appreciated by making reference to FIGS. 3A, 3B, 4A, and 4B. FIGS. 3A and 3B show multiple droplets in a microfluidic channel 301 being illuminated by three different LEDs in rapid succession during a single exposure of a camera. The droplets pass a fiducial mark 302 as they traverse the channel from left to right. Three images 303, 304, 305 of each droplet appear in the exposure, each of a different color and due to illumination by one of the LEDs. In this case, the time between LED flashes is roughly the time that it takes for a droplet to move one droplet length. FIGS. 4A and 4B show the exposure in FIGS. 3A and 3B being separated into its red, green and blue components. There is a one-to-one correspondence between the colors of the LEDs and the color filters on the camera. Therefore, the red component clearly shows an image 403 of each droplet when illuminated with the red light, and likewise for green 404 and blue 405. The three color component images can then be processed to identify the droplet locations in the microfluidic channel.

Standard image processing algorithms can be applied to images acquired in the present methods. In some embodiments, to determine a velocity of a droplet, a first centroid position of the droplet is determined in the first image, and a second centroid position of the droplet is determined in the second image. In other embodiments, the velocity is determined by determining leading or trailing edge positions of the droplet in the first and second images. To determine an inflation rate of a droplet, a change in size of the droplet between the first and second images is calculated, which can involve determining a diameter for the droplet in each image. If desired, a volume can be inferred from this diameter. Other image processing steps and algorithms will be apparent to those of skill in the art.

Image processing can be performed on-line, i.e. shortly after images are acquired, so that data on the velocities or inflation rates of droplets can be generated in real time. These data can be fed back to a microfluidic system of which the microfluidic channel is part, or presented to a user operating this system, to allow droplet handling to be tuned or optimized. Alternatively, image processing can be performed off-line, on previously acquired images.

In some embodiments, image processing algorithms return locations or sizes of a droplet in terms of pixels, in the coordinate system of the detector. These measurements can be made absolute, i.e. converted to micrometers or another unit of distance, using standard calibration techniques. Calibration can involve passing an object of known absolute size through the microfluidic channel and measuring its size in pixels. Alternatively, a pixel-to-micrometer ratio can be established with knowledge of the magnification of the system between the microfluidic channel and the detector, and/or the width of each pixel on the detector.

The velocity of the droplet passing through the microfluidic channel is determined by dividing the change in position of the droplet that occurs between acquisition of the first and second images by the amount of time allowed to pass between the acquisitions. Similarly, the inflation rate of the droplet is determined by dividing the change in size of the droplet, as determined from the two images, by this amount of time. It will be recognized that the velocity or inflation rate is an average rate of change in the position or size, respectively, of the droplet between the acquisition times. Thus, the calculated values may not fully capture irregular or non-monotonic movement or growth of the droplet. More detail about the changes in the position or size of the droplet can be obtained by imaging the droplet repeatedly, over multiple frames or exposures, for as long as the droplet remains in the field of view. More detail can also be obtained by shortening the amount of time allowed to pass between acquiring the first and second image in each frame or exposure, provided that an observable amount of change occurs over this time.

In embodiments of the system in which a pressure source is coupled to the microfluidic channel, as discussed above, the present methods can also include adjusting the pressure source based on the velocity or inflation rate of the droplet. For example, if the velocity of the droplet is measured under the present methods to be higher than desired, the pressure coupled to the microfluidic channel can be lowered to reduce the velocity of droplets passing through the microfluidic channel subsequently. Similarly, if the inflation rate of a droplet is determined to be too high, as a result of the droplet lingering for too long near a fluid source in communication with the microfluidic channel, the pressure can be raised. The pressure source can be adjusted in concert with other control parameters for any microfluidic system of which the microfluidic channel is part. Adjustment of the pressure source can be automated along with image processing and can make use of any appropriate feedback loops, algorithms, circuits, or mechanisms, such as PID control. Alternatively, the adjustment can be performed manually.

The present methods, as discussed thus far, include the acquisition of two images of a microfluidic droplet per video frame or photographic exposure, but in principle any number of images greater than or equal to two can be acquired at this time. For example, a third image can be acquired using a third flash of light, which comprises light of a third wavelength band different and distinguishable from light of the first and second wavelength bands. Thus, the frame or exposure can contain images of the droplet corresponding to three different colors, such as red, green, and blue. The number of wavelength bands that can be used in the present methods is limited only by the capacity of the detector to distinguish light of each wavelength band. When acquiring three or more images, each image can correspond to a different wavelength band, or the illumination can be performed such that a wavelength band is used more than once. In addition, a droplet can be visualized in multiple, optionally consecutive frames, such that the pattern of flashes and wavelength bands varies from one frame to the next.

In some embodiments, the method introduced above also includes the following steps: illuminating the droplet with a third flash of light emitted by the multicolor light source; acquiring a third image of the droplet when the droplet is illuminated with the third flash of light, wherein the image is acquired using the detector; selecting a reference image, wherein the reference image is either the first image or the second image; calculating an additional change in position or size of the droplet between the reference image and the third image; determining an elapsed time between acquisition of the reference image and acquisition of the third image; and dividing the additional change in position or size of the droplet by the elapsed time to determine a velocity or an inflation rate of the droplet in the microfluidic channel between the reference image and the third image.

The third image can be acquired at any time relative to the first and second images, although for simplicity it will be discussed here as being acquired after both the first and second images. In these embodiments, the reference image can be selected depending on what information is desired from acquisition of the third image. For example, if two measurements of droplet velocity are of interest, where both measurements start at the same time, then the first image can be selected as the reference image. By contrast, if measurements over different regions of the field of view are desired, then the second image can be selected as the reference image.

Regardless of which image is selected as the reference image, and whether the reference image and third image are acquired as part of the same frame, any elapsed time between acquisition of the reference and third images can be employed. In some embodiments, the elapsed time is about the same as the amount of time allowed to pass between acquisition of the first and second images of the droplet. In other embodiments, however, the elapsed time differs from this amount of time by a factor of at least two. That is, the elapsed time can be at least twice as long or less than half as long as the amount of time between acquisition of the first image and acquisition of the second image. The elapsed time can be set, imposed, or measured as desired. It will be recognized that the elapsed time is subject to practical constraints: for example, the width of the field of view puts an upper limit on the elapsed time.

Selection of the reference image and elapsed time together allows flexibility in the timescales over which measurements of droplet velocity or inflation rate are made. For example, acquisitions of the first, second, and third images can be equally spaced in time. Then two redundant measurements (one using the first and second images, and the other using the second and third images) can be made over equal spans of time as the droplet traverses the microfluidic channel. If the droplet undergoes a change in velocity or inflation rate during these measurements, then this change can be detected by comparing the measurements. On the other hand, if the droplet remains at a constant velocity or inflation rate, then the velocity or inflation rate can be known with greater certainty, as compared with a single measurement, by averaging the two measurements.

In an alternative example, the first, second, and third images can be acquired such that the time between the first and second images is relatively short and the time between the second and third images is relatively long. If the second image is taken as the reference image, then two consecutive measurements of droplet velocity or inflation rate can be made, the first over a short timescale and the second over a long timescale. These measurements can be compared to detect a change in the droplet's behavior as it traverses the microfluidic channel, or to measure constant behavior with high certainty.

The present methods can be used to measure multiple droplets in a microfluidic channel simultaneously. Multiple droplets can be visualized in a single video frame or photographic exposure, or in any number of the constituent images acquired during the frame or exposure. Any available image processing techniques can be used to distinguish between droplets and analyze images of the droplets individually. To mitigate the difficulty of identifying individual droplets, particularly when droplets move quickly or follow each other closely through the microfluidic channel, the amount of time allowed to pass between consecutive flashes of light can be reduced. Although the same droplet can be measured in successive video frames or photographic exposures, the droplet need not be tracked or identified as the same as it traverses the microfluidic channel. For example, a droplet can appear accidentally or fortuitously in two successive frames, which can be analyzed independently of each other. Measurements of droplet velocity or inflation rate can be aggregated over multiple droplets and/or multiple video frames or photographic exposures.

The present disclosure of systems and methods includes droplets passing through microfluidic channels. It will be recognized that the methods can be used to measure changes in the position or size of other objects, and indeed any object that can be illuminated and imaged as described herein. Moreover, while the inventors disclose distinguishing between flashes of light, and images acquired during these flashes of light, on the basis of wavelength, in principle this could be done using other properties of light. For example, each flash could include light of only one polarization, and the detector could distinguish between different polarizations of light. Any property of light that can take on multiple values, where the values are detectable and distinguishable from each other, can be employed.

V. Examples

A. Working Example

A high-brightness multicolor LED (red-green-blue-white) was placed below a channel in a microfluidic device and a digital color camera with two lenses was placed above the channel (FIG. 1). The multicolor LED can be conveniently customized to have light colors that closely match the color filters on the pixels of the image sensor. The multicolor LED also simplifies image analysis by having the different color emitters very close together, resulting in a similar illumination of the subject by each different color. The focal lengths and positions of the lenses were chosen to create sharp images of droplets in the channel. A stop was placed above the LED to limit the emitted light from spreading out. A second stop was placed between the two lenses to improve the image quality on the camera by increasing the camera image's depth of field at the channel. On the lens closer to the microfluidic channel, the focus was set to form an image of the LED dies at the stop between the two lenses.

Three of the four colors of the LED—red, green and blue—were used to illuminate droplets, such that the droplets could be imaged onto the camera (FIG. 2). Each of the three LED dies was flashed for a short period of time in succession, such that all three colors were flashed within the period of a single exposure of the camera. Any number of colors greater than one could achieve similar results. To minimizing background noise, each camera exposure began shortly before the first flash of the series and ended shortly after the last flash. The exposure thus had overlapping red, green, and blue images (FIGS. 3A and 3B). The total time for the series of flashes was chosen to be shorter than the time taken for a droplet to move across the field of view of the camera. The duration of each flash was chosen to be short enough that a droplet moved no more than the distance of a single camera pixel during the flash. Thus, each droplet image remained sharp and was not blurred due to motion. All three flashes in each exposure were of the same duration.

The time between the color flashes was chosen such that the droplet moved across the camera field of view by some number of pixels. The exposure thus had three images of each droplet at three discrete positions in a channel. In this example, the times between the flashes in each exposure were the same, but these can be made different to allow for a greater dynamic range of velocity measurements. Droplet velocity was estimated in order to set timing intervals for the flashes, and then exact measurements of the velocities were made.

When the exposure was separated into its red, green and blue components (FIGS. 4A and 4B), each component image had a single image of each drop. Image processing was then applied to each color component image to calculate the size and centroid position of each drop. The velocity (v) of the drop was calculated from the optical magnification (M), the width of each pixel (w), the distance in pixels that the drop moves between two successive component images (d) and the time between LED flashes (t): $v=-(w/M)*(d/t)$.

Typical color camera sensors are arrays of light sensors with sensitivity across the visible spectrum. With a pattern of color filters applied, particular pixels, sensitive only to light that passes through the filter are rendered. The most typical pattern is a repeating block of 2×2 pixels in which one pixel each is sensitive to blue and red light, and two are sensitive to green. Digitally rendered color images are most commonly rendered similarly, with three intensities per channel recorded for red, green, and blue light, which can then be reproduced on a monitor or other device for viewing. Multicolor LEDs are widely available with similar sets of red, green, and blue colored emitters. By turning on these emitters simultaneously and varying their intensities, one can use multicolor LEDs to produce light in many colors as perceived by the human eye.

In the current example, an RGB LED is flashed to excite the RGB pixels on the camera. Each exposure can be processed by the camera software and separated into its constituent RGB image planes, so extraction of the three color images is very straightforward. Generally, any set of three colors that is orthogonal with respect to the three color sensitivities of the imager can be employed. Choices other than matched red, green, and blue can be used to improve signal quality given unbalanced color sensitivities in the camera, or to exploit different filter patterns on the sensor to obtain the best possible resolution in the separated images.

B. Prophetic Example

An RGB camera with a detector that is 1000 pixels wide is used to observe a droplet traveling through a microfluidic channel. The droplet is 20 pixels wide when imaged on the detector and travels across the field of view in 0.01 second. That is, the droplet travels at 100,000 pixels per second. The camera has a minimum exposure time of 0.001 s, during which the droplet would move 100 pixels. Thus, the camera is too slow to capture a usable image of the droplet in one exposure under constant illumination. Additionally, the camera's maximum frame rate is only 100 frames per second, so the droplet would not stay in the field of view long enough to capture two exposures. Under the current methods, however, the droplet can be exposed to multiple flashes of light, each of a different wavelength band (color) and having a 10 µs duration. If the flashes are 40 µs apart, an effective frame rate of 20,000 frames/s and an effective exposure time of 10 µs are achieved. These characteristics cannot be achieved with the camera's own controls. The droplet can now be imaged at multiple positions within a single exposure, such that two or more positions are within the field of view, and the droplet does not appear blurred at any position.

VI. Computer Systems

Figure 5:
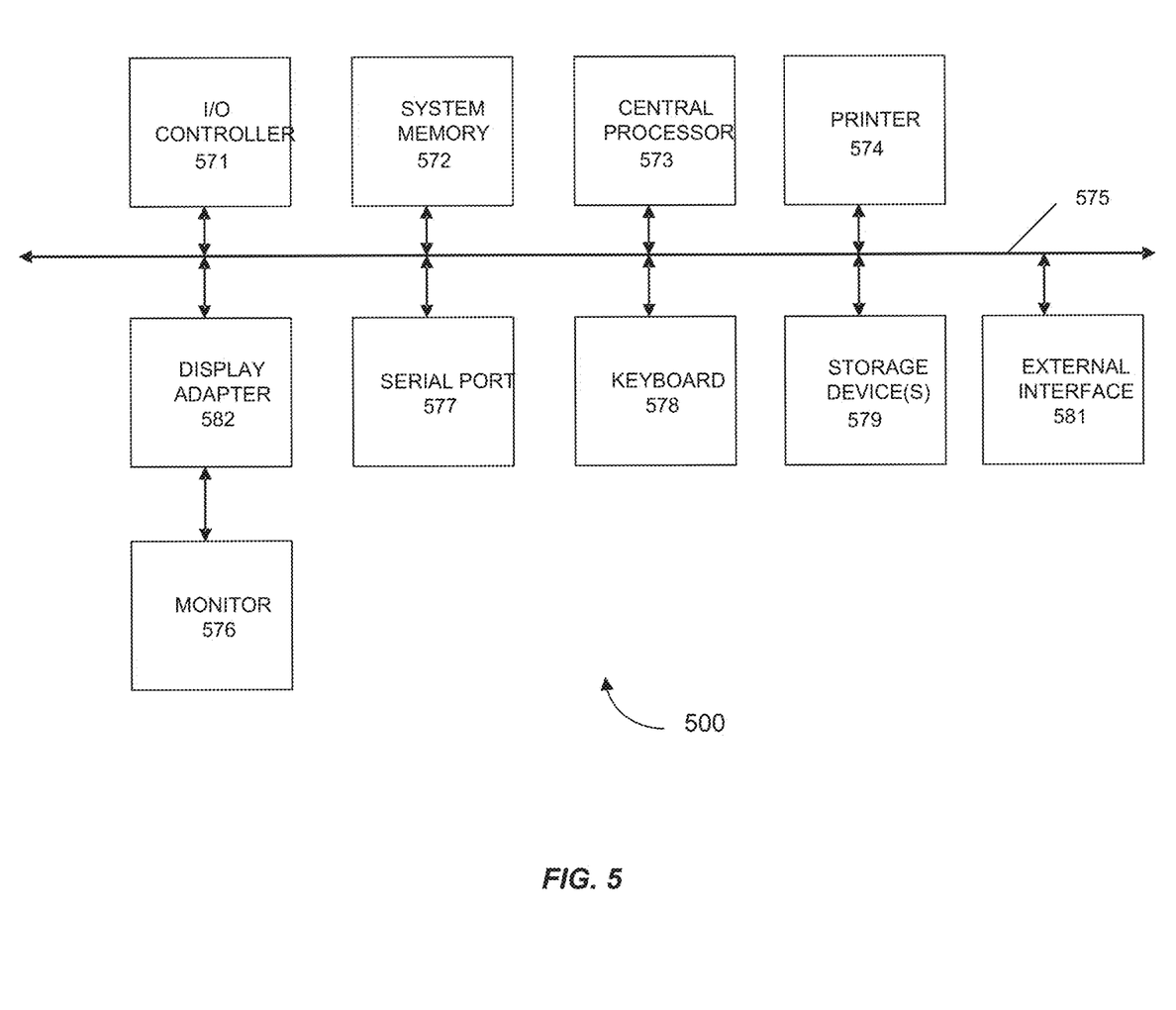
FIG. 5 shows a block diagram of a computer system 500 usable with systems and methods according to embodiments of the present invention.

Any of the computer systems mentioned herein may utilize any suitable number of subsystems. Examples of such subsystems are shown in FIG. 5 in computer apparatus 500. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 5 are interconnected via a system bus 575. Additional subsystems such as a printer 574, keyboard 578, storage device(s) 579, monitor 576, which is coupled to display adapter 582, and others are shown. Peripherals and input/output (I/O) devices, which couple to I/O controller 571, can be connected to the computer system by any number of means known in the art, such as serial port 577. For example, serial port 577 or external interface 581 (e.g. Ethernet, Wi-Fi, etc.) can be used to connect computer system 500 to a wide area network such as the Internet, a mouse input device, or a scanner. The interconnection via system bus 575 allows the central processor 573 to communicate with each subsystem and to control the execution of instructions from system memory 572 or the storage device(s) 579 (e.g., a fixed disk, such as a hard drive or optical disk), as well as the exchange of information between subsystems. The system memory 572 and/or the storage device(s) 579 may embody a computer readable medium. Any of the data mentioned herein can be output from one component to another component and can be output to the user.

A computer system can include a plurality of the same components or subsystems, e.g., connected together by external interface 581 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method for determining a velocity, an inflation rate, or both of a droplet passing through a microfluidic channel formed of a translucent material, the method comprising:

illuminating the droplet with a first flash of light emitted by a multicolor light source, wherein the multicolor light source is configured to emit light in two or more different wavelength bands and as temporally separated flashes, wherein each flash comprises light of only one of said wavelength bands, and wherein the first flash of light comprises light of a first wavelength band;

acquiring a first image of the droplet when the droplet is illuminated with the first flash of light with a detector configured to detect and distinguish between light in said wavelength bands, wherein the multicolor light source, the detector, and the microfluidic channel are positioned such that light emitted by the multicolor light source is incident upon the microfluidic channel, and the droplet passing through the microfluidic channel and illuminated by the multicolor light source is imaged on the detector;

allowing an amount of time to pass;

illuminating the droplet with a second flash of light emitted by the multicolor light source, wherein the second flash of light comprises light of a second wavelength band different from the first wavelength band;

acquiring a second image of the droplet when the droplet is illuminated with the second flash of light, wherein the first image and the second image are acquired (i) using the detector and (ii) as part of the same video frame or the same photographic exposure;

calculating a change in position of the droplet, a change in size of the droplet, or both, between the first image and the second image by separating the first image from the second image in the video frame or the photographic exposure; and dividing the change in position of the droplet, the change in size of the droplet, or both, by the amount of time, thereby determining a velocity of the droplet, an inflation rate of the droplet, or both, respectively, passing through the microfluidic channel between the first image and the second image.

2. The method of claim 1 wherein determining a velocity of the droplet further comprises calculating the change in position of the droplet by determining a first centroid position of the droplet in the first image and a second centroid position of the droplet in the second image.

3. The method of claim 1 comprising determining an inflation rate of the droplet, wherein calculating a change in size of the droplet between the first image and the second image comprises determining a first diameter of the droplet in the first image and a second diameter of the droplet in the second image.

4. The method of claim 1, wherein the system further comprises a pressure source coupled to the microfluidic channel, and the method further comprises adjusting the pressure source based upon the velocity or the inflation rate of the droplet.

5. The method of claim 1, further comprising:

illuminating the droplet with a third flash of light emitted by the multicolor light source;

acquiring a third image of the droplet when the droplet is illuminated with the third flash of light, wherein the image is acquired using the detector;

selecting a reference image, wherein the reference image is either the first image or the second image;

calculating an additional change in position of the droplet, an additional change in size of the droplet, or both, between the reference image and the third image;

determining an elapsed time between acquisition of the reference image and acquisition of the third image; and dividing the additional change in position of the droplet, the additional change in size of the droplet, or both, respectively, by the elapsed time to determine a velocity, an inflation rate, or both of the droplet in the microfluidic channel between the reference image and the third image.

6. The method of claim 5, wherein the third flash of light comprises light of a third wavelength band different from the first wavelength band and the second wavelength band.

7. The method of claim 5, wherein the third image and the reference image are acquired as part of the same video frame or the same photographic exposure.

8. The method of claim 5, wherein the elapsed time between acquisition of the reference image and acquisition of the third image differs by a factor of at least 2 from the amount of time allowed to pass between acquisition of the first image and acquisition of the second image.

9. A method for determining a velocity, an inflation rate, or both of a droplet passing through a microfluidic channel formed of a translucent material, the method comprising:

illuminating the droplet with a first flash of light emitted by a multicolor light source, wherein the multicolor light source is configured to emit light in two or more different wavelength bands and as temporally separated flashes, wherein each flash comprises light of only one of said wavelength bands, and, wherein the first flash of light comprises light of a first wavelength band;

acquiring a first image of the droplet when the droplet is illuminated with the first flash of light with a detector configured to detect and distinguish between light in said wavelength bands, wherein the multicolor light source, the detector, and the microfluidic channel are positioned such that light emitted by the multicolor light source is incident upon the microfluidic channel, and the droplet passing through the microfluidic channel and illuminated by the multicolor light source is imaged on the detector;

allowing an amount of time to pass;

illuminating the droplet with a second flash of light emitted by the multicolor light source, wherein the second flash of light comprises light of a second wavelength band different from the first wavelength band;

acquiring a second image of the droplet when the droplet is illuminated with the second flash of light, wherein the first image and the second image are acquired using the detector and as part of the same video frame or the same photographic exposure;

calculating a change in position of the droplet, a change in size of the droplet, or both, between the first image and the second image, wherein calculating the change in position of the droplet comprises determining a first centroid position of the droplet in the first image and a second centroid position of the droplet in the second image; and dividing the change in position of the droplet, the change in size of the droplet, or both, by the amount of time, thereby determining a velocity of the droplet centroid position, an inflation rate of the droplet, or both, respectively, passing through the microfluidic channel between the first image and the second image.

10. The method of claim 9, wherein calculating a change in position of the droplet or a change in size of the droplet between the first image and the second image comprises separating the first image from the second image in the video frame or the photographic exposure.

11. The method of claim 9 comprising determining an inflation rate of the droplet, wherein calculating a change in size of the droplet between the first image and the second image comprises determining a first diameter of the droplet in the first image and a second diameter of the droplet in the second image.

12. The method of claim 9, wherein the system further comprises a pressure source coupled to the microfluidic channel, and the method further comprises adjusting the pressure source based upon the velocity or the inflation rate of the droplet.

13. The method of claim 9, further comprising:
illuminating the droplet with a third flash of light emitted by the multicolor light source;
acquiring a third image of the droplet when the droplet is illuminated with the third flash of light, wherein the image is acquired using the detector;
selecting a reference image, wherein the reference image is either the first image or the second image;
calculating an additional change in position of the droplet, an additional change in size of the droplet, or both, between the reference image and the third image;
determining an elapsed time between acquisition of the reference image and acquisition of the third image; and
dividing the additional change in position of the droplet, the additional change in size of the droplet, or both, respectively, by the elapsed time to determine a velocity of the droplet, an inflation rate of the droplet, or both, in the microfluidic channel between the reference image and the third image.

14. The method of claim 13, wherein the third flash of light comprises light of a third wavelength band different from the first wavelength band and the second wavelength band.

15. The method of claim 13, wherein the third image and the reference image are acquired as part of the same video frame or the same photographic exposure.

16. The method of claim 13, wherein the elapsed time between acquisition of the reference image and acquisition of the third image differs by a factor of at least 2 from the amount of time allowed to pass between acquisition of the first image and acquisition of the second image.

17. A method for determining a velocity of a droplet, an inflation rate of a droplet, or both, passing through a microfluidic channel formed of a translucent material, the method comprising:
illuminating the droplet with a first flash of light emitted by a multicolor light source, wherein the multicolor light source is configured to emit light in two or more different wavelength bands and as temporally separated flashes, wherein each flash comprises light of only one of said wavelength bands, and, wherein the first flash of light comprises light of a first wavelength band;
acquiring a first image of the droplet when the droplet is illuminated with the first flash of light with a detector configured to detect and distinguish between light in said wavelength bands, wherein the multicolor light source, the detector, and the microfluidic channel are positioned such that light emitted by the multicolor light source is incident upon the microfluidic channel, and the droplet passing through the microfluidic channel and illuminated by the multicolor light source is imaged on the detector;
allowing an amount of time to pass;
illuminating the droplet with a second flash of light emitted by the multicolor light source, wherein the second flash of light comprises light of a second wavelength band different from the first wavelength band;
acquiring a second image of the droplet when the droplet is illuminated with the second flash of light, wherein the first image and the second image are acquired using the detector and as part of the same video frame or the same photographic exposure;
calculating a change in position of the droplet, a change in size of the droplet, or both, between the first image and the second image, wherein calculating a change in size of the droplet between the first image and the second image comprises determining a first diameter of the droplet in the first image and a second diameter of the droplet in the second image; and
dividing the change in position of the droplet, a change in size of the droplet, or both, respectively, by the amount of time, thereby determining a velocity of the droplet, an inflation rate of the droplet, or both, passing through the microfluidic channel between the first image and the second image.

18. The method of claim 17, wherein calculating a change in position of the droplet or a change in size of the droplet between the first image and the second image comprises separating the first image from the second image in the video frame or the photographic exposure.

19. The method of claim 17 wherein determining a velocity of the droplet further comprises calculating the change in position of the droplet by determining a first centroid position of the droplet in the first image and a second centroid position of the droplet in the second image.

20. The method of claim 17, wherein the system further comprises a pressure source coupled to the microfluidic channel, and the method further comprises adjusting the pressure source based upon the velocity of the droplet, the inflation rate of the droplet, or both.

21. The method of claim 17, further comprising:
illuminating the droplet with a third flash of light emitted by the multicolor light source;
acquiring a third image of the droplet when the droplet is illuminated with the third flash of light, wherein the image is acquired using the detector;
selecting a reference image, wherein the reference image is either the first image or the second image;
calculating an additional change in position or size of the droplet between the reference image and the third image;
determining an elapsed time between acquisition of the reference image and acquisition of the third image; and
dividing the additional change in position of the droplet, the additional change in size of the droplet, or both, by the elapsed time to determine a velocity of the droplet, an inflation rate of the droplet, or both, in the microfluidic channel between the reference image and the third image.

22. The method of claim 21, wherein the third flash of light comprises light of a third wavelength band different from the first wavelength band and the second wavelength band.

23. The method of claim 21, wherein the third image and the reference image are acquired as part of the same video frame or the same photographic exposure.

24. The method of claim 21, wherein the elapsed time between acquisition of the reference image and acquisition of the third image differs by a factor of at least 2 from the amount of time allowed to pass between acquisition of the first image and acquisition of the second image.

* * * * *